United States Patent [19]

Takahashi et al.

[11] Patent Number: 4,894,188

[45] Date of Patent: Jan. 16, 1990

[54] PROCESS FOR PRODUCING FATTY ACIDS AND THEIR ESTER DERIVATIVES

[75] Inventors: Takehiko Takahashi; Makoto Takagawa; Tomiyoshi Furuta, all of Niigata; Toshio Hidaka, Hiratsuka; Kazuo Takada, Niigata, all of Japan

[73] Assignee: Mitsubishi Gas Chemical Company, Inc., Tokyo, Japan

[21] Appl. No.: 700,347

[22] Filed: Feb. 13, 1985

Related U.S. Application Data

[63] Continuation of Ser. No. 507,912, Jun. 27, 1983, abandoned, which is a continuation of Ser. No. 258,529, Apr. 28, 1981, abandoned.

[30] Foreign Application Priority Data

Jun. 23, 1980 [JP] Japan ............................ 65-84916

[51] Int. Cl.$^4$ ................. C07C 67/36; C07C 67/37; C07C 67/38; C07C 51/12; C07C 51/14
[52] U.S. Cl. .................. 260/410.9 R; 260/413; 560/114; 560/232; 560/233; 562/497; 562/517; 562/519; 562/521
[58] Field of Search ............. 562/497, 519, 521, 517; 260/413, 410.9 R; 560/233, 232, 114

[56] References Cited

U.S. PATENT DOCUMENTS

| | | |
|---|---|---|
| 3,661,951 | 5/1972 | Miller, Jr. et al. ............... 562/521 |
| 3,665,034 | 5/1972 | Komatsu et al. .................. 562/521 |
| 3,962,343 | 6/1976 | Fujiyama et al. ................. 568/316 |
| 4,036,885 | 7/1977 | Fujiyama et al. ................. 568/316 |
| 4,270,983 | 6/1981 | Trivedi et al. .................... 562/521 |

FOREIGN PATENT DOCUMENTS 53-14059 5/1978 Japan.
132522 11/1978 Japan.

*Primary Examiner*—Vivian Garner
*Attorney, Agent, or Firm*—Armstrong, Nikaido, Marmelstein, Kubovcik & Murray

[57] ABSTRACT

Fatty acid and their derivatives are simply produced by reacting an olefin, carbon monoxide and water or reacting an alcohol or its derivative and carbon monoxide in the presence of a hydrogen fluoride catalyst and thermally decomposing the resulting reaction product in the presence of a lower hydrocarbon or a lower halogenated hydrocarbon.

11 Claims, No Drawings

PROCESS FOR PRODUCING FATTY ACIDS AND THEIR ESTER DERIVATIVES

This application is a continuation of application Ser. No. 507,912, filed June 27, 1983, now abandoned, which is a continuation of Ser. No. 258,529, filed Apr. 28, 1981, now abandoned.

This invention relates to a process for producing fatty acids or their derivatives by reacting an olefin, carbon monoxide and water or an alcohol or its derivative and carbon monoxide in the presence of hydrogen fluoride catalyst.

The reactions for obtaining a fatty acid having one more carbon atoms than the starting compound or a derivative of said fatty acid by reacting an olefin, carbon monoxide and water or reacting an alcohol or its derivative and carbon monoxide in the presence of an acid catalyst such as sulfuric acid, hydrogen fluoride, boron trifluoride or the like are extensively known as Koch reaction or Koch-like reaction. It is known that, when an olefin is used as starting material and hydrogen fluoride is used as the catalyst in these reactions, it is preferable to react the olefin and carbon monoxide by using substantially anhydrous hydrogen fluoride as the catalyst and then to add an equimolar or excessive quantity, to the reacted carbon monoxide, of water to produce fatty acid. It is also known that, when an alcohol or its derivative is used as the starting material, fatty acid or its derivative can be produced in a higher yield and under milder conditions by adding 1-15% by weight of water to the hydrogen fluoride in advance. That is, the reaction products of these reactions contain water in almost all cases. In such cases, the content of water is usually 1-50% by weight based on hydrogen fluoride. Since water forms a azeotropic mixture with a highest boiling point with hydrogen fluoride (hereinafter, the mixture is referred to as "hydrated catalyst") and water exhibits a strong affinity to fatty acid, it is difficult to separate the hydrated catalyst from the reaction product by merely heating the reaction product accumulated in a reactor vessel.

In order to solve such a problem, Japanese Patent Publication No. 35,722/71 proposes a process which comprises reacting an olefin with carbon monoxide, contacting the resulting reaction product with a hydrogen fluoride-water complex to give a mixture of hydrogen fluoride and a fatty acid-hydrogen fluoride complex, distilling the mixture to separate it into hydrogen fluoride and fatty acid-hydrogen fluoride complex, decomposing the fatty acid-hydrogen fluoride complex with an equimolar quantity of water and then recovering the fatty acid. However, the process involves quite complicated steps, and moreover it is expected that the concentration of fluorine remaining in the reaction product will be difficult to reduce to, for example, 0.05 moles or less per 1 mole of fatty acid merely by the process disclosed in the Japanese Patent Publication. Further, when an alcohol is used as a starting material, it is impossible to apply the process because it is not necessary to add water to the reaction product.

The present inventors have studied the method for overcoming the above-mentioned disadvantages and for separating and recovering reaction product and catalyst by a simple means. As the result, the present inventors have found a surprising fact that the separation by the thermal decomposition of fatty acid-hydrogen fluoride complex, which has hitherto been regarded as impossible or difficult, can be achieved nearly completely by feeding a reaction product into a distillation column (hereinafter referred to as "decomposition column") under reflux of hydrocarbon and decomposing it therein. The present invention was accomplished on the basis of this finding.

Thus, the invention consists in a process for producing fatty acids or their derivatives which comprises reacting an olefin, carbon monoxide and water or reacting an alcohol or its derivative and carbon monoxide in the presence of hydrogen fluoride catalyst and thermally decomposing the resulting reaction product in the presence of a lower hydrocarbon or a lower halogenated hydrocarbon.

As a starting material for producing a fatty acid or its derivative in the invention, any substance may be used so far as it is usually employed in Koch reaction or Koch-like reaction. Examples of the starting material include olefins such as ethylene, propylene, n-butylene, isobutylene, diisobutylene, nonene, hexadecene, cyclohexene and the like; alcohols such as propyl alcohol, i-butyl alcohol, t-butyl alcohol, pentyl alcohol, hexyl alcohol, octanol, 2-ethylhexanol, nonyl alcohol, dodecanol and the like; and alcohol derivatives such as methyl t-butyl ether (MTBE) and the like.

One part by mole of the starting material is contacted, either alone or together with a solvent, with 2-50 and preferably 2.5-20 parts by mole of hydrogen fluoride catalyst, and carbon monoxide under a pressure of 1-150 kg/cm$^2$, preferably 2-50 kg/cm$^2$, and at a reaction temperature of $-20°-+100°$ C., preferably $0°-80°$ C. in a reaction system. Then, after adding a necessary quantity of water thereto when olefin is used as the starting material or directly when alcohol is used as the starting material, the reaction product is fed into the decomposition column to recover the reaction product from the column bottom and the catalyst from the column top.

Since 2-50 parts by mole of hydrogen fluoride is usually used per part by mole of the starting material in the reaction, the reaction product can be supplied to the decomposition column after the hydrogen fluoride has been partly removed from the reaction product by, for example, flash distillation in advance and after that, the reaction product and the catalyst are completely separated from each other. The hydrogen fluoride recovered at the column top is recycled to the reaction system, either directly or, if necessary, after the water content has been adjusted by distillation.

In the invention, lower hydrocarbon or lower halogenated hydrocarbon (hereinafter, referred to as "decomposing agent") to be refluxed in the decomposition column is preferably the one having a boiling point lower than that of the reaction product and a solubility in hydrogen fluoride being not so high. Those suitable for the above-mentioned conditions include aliphatic hydrocarbons having 2-6 carbon atoms and their halogenated products such as butane, pentane, hexane, dichlorethane, chloropropane and chlorobutane; and aromatic hydrocarbons having 6-8 carbon atoms and their halogenated products such as benzene, toluene, xylene, chlorobenzene, chlorotoluene, fluorobenzene, fluorotoluene and the like. Aliphatic hydrocarbons having many carbon atoms such as heptane are undesirable because they have a tendency of somewhat decreasing the recovery ratio of the fatty acid formed.

The decomposition pressure though it depends upon other steps and is not particularly limited, practically preferably is in the range of 1–10 kg/cm² (absolute). The decomposition temperature, though it depends upon various factors such as decomposition pressure, the kind of decomposing agent, the concentration of reaction product, etc., is 50°–230° C. for the column bottom, 30°–140° C. for the level at which the reaction product is supplied and 10°–90° C. for the column top, according to the studies made by the inventors. The heat quantity to be supplied to the decomposition column is preferably at least 1.05 times the sum total of the latent heat required for vaporizing hydrogen fluoride and hydrated catalyst and the sensible heat required for heating reaction product and the like (hereinafter, the sum total will be referred to as "theoretical heat quantity"). The larger the ratio to theoretical heat quantity (=supplied heat quantity÷theoretical heat quantity), the lower the concentration of fluorine in the reaction product recovered from the column bottom. However, excessive heat will be consumed. Therefore, the ratio to theoretical heat quantity must be determined from the economic point of view. The decomposition column preferably has the theoretical number of plates of at least 2. If the theoretical number of plates is too small, a portion of the reaction product distills off the column top.

When a reaction product is thermally decomposed in the above-mentioned ranges of operating conditions, the recovery ratio of fatty acid is 97–100% and the concentration of residual fluorine is 0.0002–0.02 moles per mole of fatty acid.

The decomposition column to be used in the invention can be a distillation column hitherto known, such as packed column, tray column and the like.

The reaction product can be supplied batchwise or continuously.

EXAMPLE

A packed column having an inner diameter of 35 mm and a column height of 800 mm, packed with 6 mm Dixon packings in its inside and equipped with an overhead condenser and a separation tank is used as a decomposition column.

The decomposition pressure ranges from atmospheric pressure to 5 kg/cm² (absolute), and the inner pressure of column is maintained by continuously supplying a small quantity of nitrogen into the decomposition column and releasing the excessive nitrogen by adjusting the electro-magnetic valve. A decomposing agent such as pentane, hexane, benzene or the like is refluxed into the decomposition column in advance and reaction product is continuously supplied to the middle level or lower level of the column. The catalyst is withdrawn from the decomposition chamber at the column top and the reaction product is withdrawn from the column bottom, both continuously. Heating is carried out by electric heating.

The reaction product supplied to the decomposition column is a solution containing pivalic acid, methyl pivalate, isononanoic acid or the like, prepared from i-butanol, t-butanol, methyl t-butyl ether or diisobutylene in the presence of hydrogen fluoride as a catalyst.

When an olefin is used as the starting material, the reaction is carried out by using substantially anhydrous hydrogen fluoride and, after the reaction, water is added in an amount of 1.3 moles per mole of the carbon monoxide absorbed upon the reaction, and then the resulting reaction product is supplied to the decomposition column.

When an alcohol or its derivative is used as the starting material, hydrogen fluoride containing 2–15% by weight of water is used as the catalyst and directly supplied to the decomposition column. The catalyst recovered from the decomposition column is reused in the reaction system either directly or after being dehydrated by redistillation. The conditions of the reaction system and the results of the decomposition are shown in Table 1 and Table 2.

TABLE 1

| | Example No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Starting material | i-Butanol | i-Butanol | t-Butanol | t-Butanol | t-Butanol | t-Butanol | Iso-butylene | MTBE | Diisobutylene | t-Butanol | t-Butanol | t-Butanol |
| Reaction temperature (°C.) | 65 | 65 | 50 | 50 | 50 | 50 | 30 | 50 | 30 | 50 | 50 | 50 |
| Reaction pressure (kg/cm²) | 7.5 | 7.5 | 7.5 | 7.5 | 7.5 | 7.5 | 70 | 10 | 6 | 7.5 | 7.5 | 7.5 |
| Reaction time (hr) | 3.0 | 3.0 | 2.5 | 1.3 | 1.0 | 1.0 | 3 | 2.3 | 1.1 | 1.0 | 1.0 | 1.0 |
| HF/Starting material (by mole) | 19 | 20 | 5.5 | 5.5 | 11 | 11 | 11 | 5.5 | 11.5 | 11 | 11 | 11 |
| Water/HF (by weight) | 0.02 | 0.03 | 0.05 | 0.07 | 0.02 | 0.02 | 0.05 | 0.02 | 0 | 0.02 | 0.02 | 0.02 |

TABLE 2

| | Example No. | | | | | | |
|---|---|---|---|---|---|---|---|
| | 1 | 2 | 3 | 4 | 5 | 6 | 7 |
| Reaction product supplied to decomposition column | Pivalic acid | Pivalic acid | Pivalic acid | Pivalic acid | Pivalic acid | Pivalic acid | Pivalic acid Isononanoic acid |

TABLE 2-continued

| | | | | | | | | |
|---|---|---|---|---|---|---|---|---|
| Reaction product | HF (g/hr) | 483 | 274 | 354 | 180 | 370 | 363 | 570 |
| | Water (") | 12 | 8 | 18 | 14 | 7 | 7 | 29 |
| | Fatty acid (or ester) (") | 121 | 58 | 313 | 123 | 164 | 162 | 245 |
| Conditons of decompositon | Decomposition pressure (kg/cm² gage) | 0 | 0 | 2.1 | 2.0 | 2.0 | 4.1 | 4.0 |
| | Decomposing agent | Hexane | Toluene | Hexane | Benzene | Hexane | Pentane | Hexane |
| | Ratio to theoretical heat quantity*¹ | 1.3 | 3.4 | 5.7 | 2.3 | 1.3 | 2.4 | 1.8 |
| Overhead gas | Recovery ratio of HF (%) | 98.2 | 99.3 | 98.7 | 98.8 | 99.6 | 98.3 | 98.1 |
| | Recovery ratio of water (%) | 97.6 | 99.4 | 98.3 | 97.1 | 98.3 | 99.3 | 98.6 |
| | Recovery ratio of fatty acid (or ester) (%) | 99.7 | 98.9 | 99.1 | 99.8 | 99.3 | 98.4 | 98.3 |
| Bottom liquid | Concentration of residual fluorine (by mole)*² | 0.015 | 0.002 | 0.0002 | 0.008 | 0.018 | 0.010 | 0.011 |

| | | Example No. | | | | |
|---|---|---|---|---|---|---|
| | | 8 | 9 | 10 | 11 | 12 |
| Reaction product supplied to decomposition column | | Methyl pivalate | Isononanoic acid Pivalic acid | Pivalic acid | Pivalic acid | Pivalic acid |
| Reaction product | HF (g/hr) | 215 | 350 | 368 | 370 | 367 |
| | Water (") | 4 | 22 | 7 | 7 | 7 |
| | Fatty acid (or ester) (") | 206 | 184 | 163 | 164 | 163 |
| Conditons of decompositon | Decomposition pressure (kg/cm² gage) | 2.0 | 2.0 | 2.0 | 2.0 | 2.0 |
| | Decomposing agent | Hexane | Hexane | Monofluorobenzene | p-Chlorotoluene | Monochloropropane |
| | Ratio to theoretical heat quantity*¹ | 1.1 | 3.5 | 1.5 | 1.7 | 1.3 |
| Overhead gas | Recovery ratio of HF (%) | 98.7 | 98.3 | 99.1 | 99.6 | 98.4 |
| | Recovery ratio of water (%) | 98.7 | 98.4 | 97.3 | 98.6 | 99.4 |
| | Recovery ratio of fatty acid (or ester) (%) | 98.5 | 97.2 | 99.4 | 98.9 | 98.7 |
| Bottom liquid | Concentration of residual fluorine (by mole)*² | 0.017 | 0.003 | 0.016 | 0.011 | 0.020 |

*¹(Heat input at column bottom) ÷ (Heat quantity required for evaporating hydrogen fluoride and water in reaction product)
*²(Fluorine expresed as HF/Fatty acid or ester) (mole/mole)

What is claimed is:

1. In a process for producing fatty acids and their esters which comprises reacting an olefin, carbon monoxide and water in the presence of a hydrogen fluoride catalyst, or reacting an alcohol or its ether and carbon monoxide in the presence of a hydrogen fluoride catalyst containing water, and thermally decomposing the resulting reaction product containing water, the improvement comprising conducting the thermal decomposition under reflux of at least one hydrocarbon or halogenated hydrocarbon having a boiling point lower than the reaction product and being selected from the group consisting of aliphatic hydrocarbons having 2–6 carbon atoms, halogenated aliphatic hydrocarbons having 2–6 carbon atoms, aromatic hydrocarbons having 6–8 carbon atoms and halogenated aromatic hydrocarbons having 6–8 carbon atoms, whereby the reaction product of fatty acid or its ester has 0.05 or less mole of fluorine per mole of fatty acid or its ester.

2. A process according to claim 1, wherein the olefin is ethylene, propylene, n-butylene, isobutylene, diisobutylene, nonene, hexadecene, or cyclohexene.

3. A process according to claim 1, wherein the alcohol is propyl alcohol, i-butyl alcohol, t-butyl alcohol, pentyl alcohol, hexyl alcohol, octanol, 2-ethylhexanol, nonyl alcohol, or dodecanol.

4. A process according to claim 1, wherein the ether is methyl-t-butyl ether.

5. A process according to claim 1 wherein 2–50 moles of the hydrogen fluoride catalyst is used per mole of the olefin, the alcohol or its ether, the reaction system is saturated with carbon monoxide under a carbon monoxide pressure of 1–50 kg/cm² and reaction temperature is −20°–100° C.

6. A process according to claim 1, wherein the reaction product is admixed with a necessary amount of water before the decomposition when the olefin is used.

7. A process according to claim 1 wherein the aliphatic hydrocarbon, the halogenated aliphatic hydrocarbon, the aromatic hydrocarbon or the halogenated aromatic hydrocarbon is butane, pentane, hexane, dichloroethane, chloropropane, chlorobutane, benzene, toluene, xylene, chlorobenzene, chlorotoluene, fluorobenzene, or fluorotoluene.

8. A process according to claim 1, wherein the decomposition of the reaction product is carried out in a decomposition column under a pressure of 1–10 kg/cm² absolute at 50°–230° C. for column bottom, 30°–140° C. for level at which the reaction product is supplied, and 10°–90° C. for column top.

9. A process according to claim 8, wherein the decomposition column has a theoretical number of plates of at least 2.

10. A process according to claim 8, wherein the reaction product is recovered at the decomposition column's bottom and the hydrogen fluoride catalyst is recovered at the decomposition column's top and recycled to the reaction system.

11. A process according to claim 1, wherein the reaction product of fatty acid or its ester has a concentration of residual fluorine of 0.0002–0.02 moles per mole of fatty acid or its ester.

* * * * *